United States Statutory Invention Registration [19]

[11] Reg. Number: H74

Shiue et al. [45] Published: Jun. 3, 1986

[54] PROCESS FOR THE PRODUCTION OF 18F-2-DEOXY-2-FLUORO-D-GLUCOSE

[75] Inventors: Chyng-Yann Shiue, East Setauket, N.Y.; Piero A. Salvadori, Pisa, Italy; Alfred P. Wolf, Setauket, N.Y.; Joanna S. Fowler, Bellport, N.Y.; Robert R. MacGregor, Sag Harbor, N.Y.

[73] Assignee: The United States of America as represented by The United States Department of Energy

[21] Appl. No.: 469,597

[22] Filed: Feb. 24, 1983

[51] Int. Cl.[4] ..... C07H 1/00; C07H 5/02; C07H 5/00

[52] U.S. Cl. ..... 536/124; 536/122; 536/18.4; 536/18.5

[58] Field of Search ..... 536/18.1, 18.4, 4.1

[56] References Cited

PUBLICATIONS

Ido et al., *J. Org. Chem.* 43:2341 (1977).
Ido et al. *J. Label. Cmpds. Radiopharm.* 14:175 (1978).
Rozen et al., *J.C.S. Chem. Comm.* 443 (1981).
Barrio et al., *J. Nucl. Med.* 22:372 (1981).
Shiue et al., *J. Nucl. Med.* 23:899 (1982).
Levy et al., *Abstract Book of the Society of Nuclear Medicine,* 29th Annual Meeting, Jun. 15–18, 1982 p. 107.
Shiue et al., *Abstract Book of the Society of Nuclear Medicine,* 29th Annual Meeting, Jun. 15–18, 1982, pp. 108–109.
Tewson et al., *Abstract Book of the Society of Nuclear Medicine,* 29th Annual Meeting, Jun. 15–18, 1982, p. 109.
Shiue et al, *Proceedings of the Third World Congress of Nuclear Medicine and Biology,* pp. 2125–2129 (1982).
Fowler et al., Abstract, *Fourth International Symposium on Radiopharmaceutical Chemistry,* (1982).
Szareh et al. *J. Chem. Soc. Chem. Comm.* 1253 (1982).
Rozen et al., J. C. S. Chem. Comm. 443 (1981).

*Primary Examiner*—John F. Terapane
*Assistant Examiner*—Jack Thomas
*Attorney, Agent, or Firm*—Margaret C. Bogosian; Paul A. Gottlieb; Judson R. Hightower

[57] ABSTRACT

Process for the production of 2-deoxy-2-fluoro-D-glucose and the corresponding $^{18}$F-compound by the reaction of acetyl hypofluorite or the corresponding $^{18}$F-compound with 3,4,6-tri-O-acetyl-D-glucal followed by hydrolysis. Process includes the production of the hypofluorite compound at ambient temperature.

3 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR THE PRODUCTION OF 18F-2-DEOXY-2-FLUORO-D-GLUCOSE

BACKGROUND OF THE INVENTION

The United States Government has rights to this invention pursuant to Contract Number DE-AC02-76CH00016 between the United States Department of Energy and Associated Universities, Inc.

This invention relates to 2-deoxy-2-[$^{18}$F]fluoro-D-glucose ($^{18}$FDG) and to methods of preparing it. More particularly, it relates to novel procedures for the preparation of this known compound.

The development of a rapid synthetic procedure to $^{18}$FDG using $^{18}$F-labeled elemental flourine ([$^{18}$F]$F_2$) coupled with the development of positron emission transaxial tomography (PETT) and appropriate mathematical models has made it possible to measure local cerebral glucose metabolism in man non-invasively. This has generated intense interest in the biomedical community in the use of $^{18}$FDG and PETT to study the correlation of metabolism and function in a variety of human pathologies as well as normal activity.

As a result of this interest, many cyclotron (accelerator)-PETT centers have instituted, or are in the process of instituting, the targetry and synthesis system required for producing this radiotracer. These $^{18}$FDG synthesis systems have been based on minor modifications of the $^{18}$FDG synthesis originally reported by Ido et al., *J. Org. Chem.* 42: 2341 (1977) and *J. Label. Cmpds. Radiopharm.* 14: 175 (1978). A major problem in meeting increasing demands for this tracer is that many cyclotron-PETT centers have medical cyclotrons which do not have the optimal deuteron energies for $^{18}$F production via the $^{20}$Ne(d,α)$^{18}$F reaction described by Casella et al., *J. Nucl. Med.* 21: 750 (1980). This, together with the low chemical yield from the original $^{18}$FDG synthesis (about 10%) imposes a limitation on the capabilities of many centers to synthesize sufficient $^{18}$FDG for their own needs and has necessitated the supply of $^{18}$FDG from centers where it can be produced to institutions using the tracer product which are located within a 2 to 3 hour shipping radius. It is apparent then, that the development of an improved synthesis of $^{18}$FDG would make it possible for institutions with small medical cyclotrons or other accelerators to produce sufficient quantities of $^{18}$FDG for their own daily use and would allow the production of multiple dose batches of $^{18}$FDG by institutions with cyclotrons of higher production capacity.

THE INVENTION

A procedure has now been discovered for the preparation of $^{18}$FDG which permits the rapid, facile production of this compound in highly purified form at a yield which is generally about double the yield which can be achieved with the conventional method.

In accordance with the invention, $^{18}$FDG is produced by the reaction of 3,4,6-tri-O-acetyl-D-glucal (TAG) with $^{18}$F-labeled acetyl hypofluorite, $CH_3COO^{18}F$, followed by acid hydrolysis. The latter compound is produced from [$^{18}$F]$F_2$ by a novel method.

The production of acetyl hypofluorite was first described by Rozen et al., *J.C.S. Chem. Comm.* 443 (1981). The procedure employed was to react nitrogen diluted fluorine with sodium acetate and acetic acid in trichloromonofluoromethane at −78° C. It has now been discovered that acetyl hypofluorite can be prepared at ambient temperature, e.g. 20° to 40° without the use of a halogenated hydrocarbon solvent. In the process, fluorine in a reaction inert gas such as nitrogen or neon is passed into a mixture of acetic acid and a molar excess of alkali metal, alkaline earth metal or ammonium salt of acetic acid at ambient temperature and the mixture held at the selected temperature for 20 to 40 minutes to produce the desired product. The product is normally not isolated but is utilized in situ.

The yield of product may be determined by adding an aliquot of the solution to excess KI solution and titrating the liberated iodine with sodium thiosulfate. The chemical yield is normally about 80%. The radiochemical yield is about one half of that value since each molecule of fluorine produces one molecule of fluoride salt in addition to the acetyl hypofluorite.

The presently preferred reagent is ammonium acetate which is conveniently generated by the addition of ammonium hydroxide to acetic acid.

The following table shows typical yields of acetyl hypofluorite with various acetate salts in acetic acid utilizing a mixture of fluorine and neon.

TABLE I

| Cation | Reaction time | Yield of $CH_3COOF$ |
|---|---|---|
| $Na^+$ | 13 | 52% |
| $Na^+$ | 23 | 64% |
| $Na^+$ | 46 | 67% |
| $NH_4^+$ | 23 | 79% |
| $K^+$ | 23 | 77% |
| $Cs^+$ | 23 | 71% |
| None | 23 | 44% |

The $^{18}$F-acetyl hypofluorite is converted to $^{18}$FDG by reaction with TAG, preferably a slight molar excess to insure complete reaction, followed by hydrolysis of the acetyl groups. The preferred procedure is to add TAG to the solution containing the $^{18}$F-acetyl hypofluorite. The reaction is spontaneous, starts immediately and goes rapidly to completion.

The intermediate 2-deoxy-2-[$^{18}$F]-fluoro-1,3,4,6-tetra-O-acetyl-α-D-glucopyranose may be isolated, but is normally hydrolyzed to $^{18}$FDG with dilute aqueous acid, for example, 1 to 2.5N hydrochloric acid at 100° C. to 135° C. for 10 to 20 minutes. Other acids can be employed, preferably dilute inorganic acids such as sulfuric acid.

The product can be isolated by any convenient procedure such as chromatography as illustrated in the examples. The yield by the presently preferred methods is about 20%, a factor of 2 higher than the previous synthesis.

This invention has been described with reference to acetyl substituted compounds since these are most readily available, inexpensive and convenient to use. Those skilled in the art will recognize that the reactions are general ones and that compounds substituted with other acyl groups can be employed.

EXAMPLE I

Synthesis of $CH_3COO^{18}F$ from [$^{18}$F]$F_2$

[$^{18}$F]$F_2$ (30 to 40 μmol) prepared by the procedure of Casella et al., cited above, was purged from the target through a glass reaction vessel containing a solution of ammonium hydroxide (58%, 0.010 ml) in acetic acid (15 ml) over a period of 25 minutes to give a solution of $CH_3CO_2{}^{18}F$. The vessel (0.43 in I.D.×9 in. high) was fitted with a Teflon frit (0.43 in. diameter) through which 12 small holes (0.0145 in.) were drilled. This design provided efficient gas dispersal.

The yield of $CH_3CO_2{}^{18}F$ produced by this method was determined by transferring the acetic acid solution into excess of 1 M KI solution and titrating the liberated $I_2$ with 0.01 N $Na_2S_2O_3$. The chemical yield was 80% (24–32 μmol) and the radiochemical yield was 40%. For the synthesis of $^{18}$FDG, the acetic acid solution containing $CH_3CO_2{}^{18}F$ was used immediately after purging of the target contents was completed.

EXAMPLE II

Synthesis of 2-deoxy-2-[$^{18}$F]fluoro-D-glucose From $^{18}$F-labeled Acetyl Hypofluorite To a solution of the hypofluorite (24–32 μmol) prepared as described above was added 25 mg of TAG in 1 ml of acetic acid. This solution was evaporated to dryness, 3 ml of 2 N HCl was added and the mixture heated at 120° for 12 min. Activated charcoal (10 mg) was added, the acid was evaporated, 3 ml of aqueous acetonitrile (0.3% $H_2O$) added and the mixture transferred to a column (0.75×10 cm) of silica gel (Merck No. 9385) followed by a 2 ml rinse with the same solvent, a forecut (6.5 ml) taken and discarded and the product eluted with about 15 ml of solvent. The solvent was evaporated, 1 ml of $H_2O$ (USP) added and this was also evaporated. Saline was added and the solution passed through a millipore filter (0.22 μm). Thin layer chromatography ($CH_3CN$:$H_2O$, 95:5) showed the product to have a radiochemical purity of 98%, the impurities probably being partially hydrolyzed, 2-deoxy-2-[$^{18}$F]fluoro-1,3,4,6-tetra-O-acetyl-α-D-glucopyranose. The methylsilyl derivative and radiogas chromatography of the product as described in Sweeley et al., *J. Am. Chem. Soc.* 85, 2497–2507 (1963) showed the radioactivity to be congruent with the mass peaks corresponding to the silylated α- and β- anomers of 2-$^{18}$FDG. HPLC (Bio-Rad HPLC carbohydrate analysis column, 85° C. $H_2O$, flow 0.6 ml/min) also confirmed the identity of the product as 2-$^{18}$FDG with retention time of 8 min.

The absence of 2-deoxy-2-[$^{18}$F]fluoro-D-mannose (2-$^{18}$FDM) was verified by synthesizing this compound independently from 2-deoxy-2-fluoro-3,4,6-tri-O-acetyl-β-D-mannopyranosyl fluoride by the method of Ido et al., cited above, forming its trimethylsilyl derivative and analyzing by glc (10% SE-30, 6 ft.×1/8 in.; flow 20 ml/min; 180°). The retention times of the silylated derivatives of 2-FDG were 24 min (α) and 30 min (β), while the retention times of 2-FDM derivatives were 25 min (α) and 34 min (β).

From 24–32 μmol of acetyl hypofluorite used in this synthesis, 12–16 μmol (2.2–2.9 mg, 50% chemical yield) of 2-FDG is produced. The radiochemical yield is 20% based on total $^{18}$F recovered from the target. Thus from 350 mCi of $^{18}$F, 45 mCi of 2-$^{18}$FDG is obtained at the end of a 70 minutes synthesis (EOS). This corresponds to a specific activity of 15.5–20.5 mCi/mg at EOS.

What is claimed is:

1. A process for the production of $^{18}$F-2-deoxy-2-fluoro-D-glucose in yields of about 20% based on total $^{18}$F which comprises reacting $^{18}$F-acetyl hypofluorite with 3,4,6-tri-O-acetyl-D-glucal and thereafter hydrolyzing the resulting tetraacetyl compound in dilute aqueous acid to remove the acetyl groups.

2. A process for the production of $^{18}$F-2-deoxy-2-fluoro-D-glucose which comprises the steps of:

1. reacting $F_2$ in a reaction inert gas with acetic acid and a molar excess of an alkali metal, alkaline earth metal or ammonium salt of acetic acid at a temperature of from 20° to 40° C. for from 20 to 40 minutes,
2. adding 3,4,6-tri-O-acetyl-D-glucal and allowing the mixture to react, and
3. hydrolyzing the resulting tetraacetyl compound in dilute aqueous acid to remove the acetyl groups.

3. A process as in claim 2 wherein the acetic acid salt is ammonium acetate.

* * * * *